(12) United States Patent
Shen

(10) Patent No.: US 9,260,404 B1
(45) Date of Patent: Feb. 16, 2016

(54) **PREPARATION OF AMBROX FROM LABDANES OF *DYSOXYLUM HONGKONGENSE*, AND THE PREPARATION OF NEW DITERPENOIDS FROM *DYSOXYLUM HONGKONGENSE***

(71) Applicant: National Taiwan University, Taipei (TW)

(72) Inventor: Ya-Ching Shen, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 14/548,374

(22) Filed: Nov. 20, 2014

(30) Foreign Application Priority Data

Aug. 12, 2014 (TW) .............................. 103127686 A

(51) Int. Cl.
*C07D 307/92* (2006.01)
*C07C 45/78* (2006.01)
*C07C 49/743* (2006.01)

(52) U.S. Cl.
CPC .............. *C07D 307/92* (2013.01); *C07C 45/78* (2013.01); *C07C 49/743* (2013.01); *C07C 2102/28* (2013.01)

(58) Field of Classification Search
CPC ...... C07D 307/92; C07C 45/07; C07C 45/08; C07C 49/74; C07C 49/03; C07C 2102/28
See application file for complete search history.

(56) References Cited

U.S. PATENT DOCUMENTS

| | | | |
|---|---|---|---|
| 5,290,955 A | 3/1994 | Asanuma et al. | |
| 5,463,089 A | 10/1995 | Barton et al. | |
| 2012/0301956 A1 | 11/2012 | Rahman et al. | |
| 2014/0199741 A1* | 7/2014 | Carey ............................ | 435/156 |

FOREIGN PATENT DOCUMENTS

| | | | |
|---|---|---|---|
| ES | 2195777 A1 * | 12/2003 | ........... C07D 307/92 |
| WO | 2012/085056 | 6/2012 | |

OTHER PUBLICATIONS

Zhang, Q.,"Dammarane triterpenoids from Dysoxylum hongkongense." Acta Botanica Yunnanica 20.3 (1997): 362-368.*
Zoretic et al. "Synthesis of d.l-Norlabdane oxide and related odorants: an intramolecular radical approach" J. Org. Chem., 1998, 63(14): 4779-4785.
Kuo et al. Samaragnenin B from limonium sinesse suppresses herpes simplex virus type 1 replication in vero cells by regulation of viral macromelecular synthesis: Antimicrob. Agents Chemother., 2002, 46(9): 2854-2864.
Hwang et al., Inhibition os superoxide anion and elastase release in human neutrophils by 3'-isopropoxychalcone via a cAMP-dependent pathway. Br. J Pharmacol., 2006, 148(1): 78-87.
Liaw et al., Frajunolides E-K, Briarane Diterpenes from Junceela fragilis. J. Nat. Prod., 2008, 71(9): 1551-1556.

* cited by examiner

*Primary Examiner* — Samantha Shterengarts
*Assistant Examiner* — Matt Mauro

(57) ABSTRACT

The present invention discloses eight new diterpenoids, i.e. Dysongensins A to H, extracted from the leaves and twigs of *Dysoxylurn hongkongense*, wherein AMBROX® which is applicable in the perfume industry is prepared from Dysongensin A via a series of chemical reactions, and the cytotoxicity of Dysongensins A to H against human cancer cell lines and their antiviral and anti-inflammatory activities are determined. Therefore, in the present invention, AMBROX® prepared from Dysongensin A is a new idea for application as an odorous compound in the perfume industry, and the novel diterpenoids can be prepared as a pharmaceutical compositions and/or a drug having antiviral, anti-inflammatory and/or anti-cancer activities.

10 Claims, 4 Drawing Sheets

PREPARATION OF AMBROX FROM LABDANES OF *DYSOXYLUM HONGKONGENSE*, AND THE PREPARATION OF NEW DITERPENOIDS FROM *DYSOXYLUM HONGKONGENSE*

CROSS-REFERENCE TO RELATED APPLICATION AND CLAIM OF PRIORITY

This application claims the benefit of Taiwan Patent Application No. 103127686, filed on Aug. 12, 2014, at the Taiwan Intellectual Property Office, the disclosures of which are incorporated herein in their entirety by reference.

FIELD OF THE INVENTION

The present invention relates to a preparation method for AMBROX® ((−)-3a,6,6,9a-tetramethyl-dodecahydronaphtho[2,1-b]furan), and new compounds which are extracted from *Dysoxylum honkongense* and used for anti-virus, anti-inflammation or anti-cancer treatments, as well as pharmaceutical compositions and drugs thereof.

BACKGROUND OF THE INVENTION

Ambergris is a solid wax, which is formed from excretions of the sperm whale, *Physeter macrocephalus* L. (Physeteridae), via a bacterial and enzymatic process. It has been known that the odorous compound AMBROX® (a registered trademark name of Firmemich SA, Geneva, Switzerland), a naturally occurring triterpenoid with wide perfume applications in industry, can be obtained from ambergris. However, because it is difficult to obtain ambergris from endangered sperm whales at present the availability, ambergris and natural AMBROX® are largely The current techniques to obtain AMBROX® are via chemical synthesis. For instance, U.S. Pat. Nos. 5,290,955 and 5,463,089, as well as WIPO Patent Publication No. WO 2012/085056 A1 disclose methods for chemically synthesizing AMBROX® (i.e. (−)-3a,6,6,9a-tetramethyl-dodecahydronaphtho[2,1-b]furan), which are incorporated herein by reference. In addition, U.S. Patent Publication No. US 2012/0301956 A1 discloses that polar hydroxylated enantiomers of ambrox can be prepared using a microbial fermentation technique using a fungi, *Fusarium lini*, and offer new highly prized odiferous characteristics quite different from ambrox and can be used in the preparation of perfumes, odor-masking and other odor-management applications, and the full text is incorporated herein by reference.

It is therefore the Applicant's attempt to deal with the above situation encountered in the prior art.

SUMMARY OF THE INVENTION

To search for a novel preparation method for AMBROX® that can be applied in the perfume industry, a diterpenoid of formula (I) (see below, a type of labdanes) of the present invention is extracted from a native plant, *Dysoxylum hongkongense* (Maliaceae), in Taiwan, and AMBROX® is synthesized from the diterpenoid of formula (I) via a series of chemical reactions. In addition, the present invention also discloses that new diterpenoids are extracted from *D. hongkongense*, and may be used to prepare pharmaceutical compositions for anti-virus, anti-inflammation or anti-cancer treatments, and drugs used therefore may be further manufactured from the pharmaceutical compositions.

The compounds and their chemical formulae in the present invention are illustrated as follows.

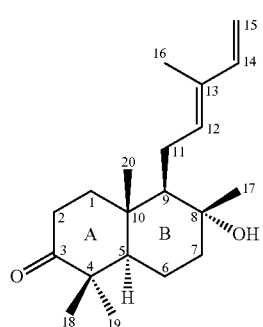

(formula (I))

compound 1

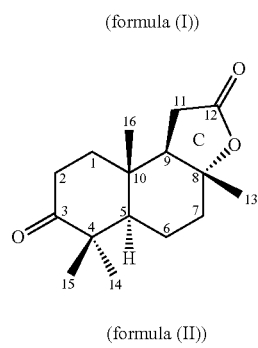

(formula (II))

compound 2

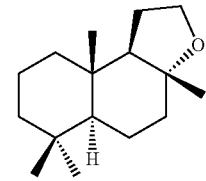

(formula (III))

compound 3

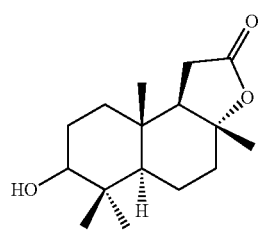

compound 4

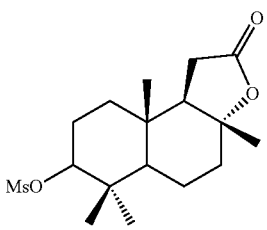

compound 5

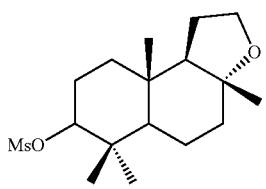

compound 6

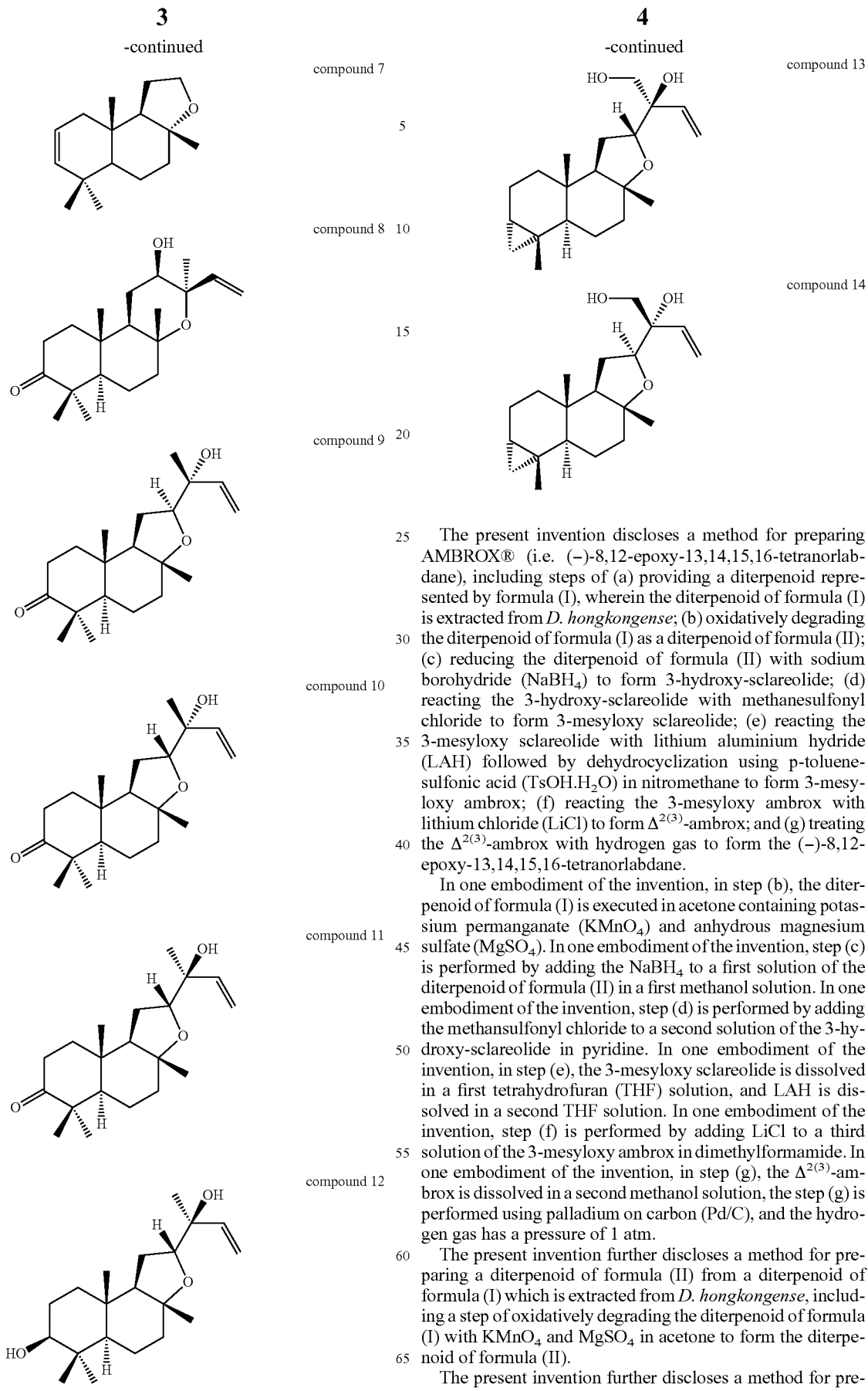

The present invention discloses a method for preparing AMBROX® (i.e. (−)-8,12-epoxy-13,14,15,16-tetranorlabdane), including steps of (a) providing a diterpenoid represented by formula (I), wherein the diterpenoid of formula (I) is extracted from *D. hongkongense*; (b) oxidatively degrading the diterpenoid of formula (I) as a diterpenoid of formula (II); (c) reducing the diterpenoid of formula (II) with sodium borohydride (NaBH$_4$) to form 3-hydroxy-sclareolide; (d) reacting the 3-hydroxy-sclareolide with methanesulfonyl chloride to form 3-mesyloxy sclareolide; (e) reacting the 3-mesyloxy sclareolide with lithium aluminium hydride (LAH) followed by dehydrocyclization using p-toluenesulfonic acid (TsOH.H$_2$O) in nitromethane to form 3-mesyloxy ambrox; (f) reacting the 3-mesyloxy ambrox with lithium chloride (LiCl) to form $\Delta^{2(3)}$-ambrox; and (g) treating the $\Delta^{2(3)}$-ambrox with hydrogen gas to form the (−)-8,12-epoxy-13,14,15,16-tetranorlabdane.

In one embodiment of the invention, in step (b), the diterpenoid of formula (I) is executed in acetone containing potassium permanganate (KMnO$_4$) and anhydrous magnesium sulfate (MgSO$_4$). In one embodiment of the invention, step (c) is performed by adding the NaBH$_4$ to a first solution of the diterpenoid of formula (II) in a first methanol solution. In one embodiment of the invention, step (d) is performed by adding the methansulfonyl chloride to a second solution of the 3-hydroxy-sclareolide in pyridine. In one embodiment of the invention, in step (e), the 3-mesyloxy sclareolide is dissolved in a first tetrahydrofuran (THF) solution, and LAH is dissolved in a second THF solution. In one embodiment of the invention, step (f) is performed by adding LiCl to a third solution of the 3-mesyloxy ambrox in dimethylformamide. In one embodiment of the invention, in step (g), the $\Delta^{2(3)}$-ambrox is dissolved in a second methanol solution, the step (g) is performed using palladium on carbon (Pd/C), and the hydrogen gas has a pressure of 1 atm.

The present invention further discloses a method for preparing a diterpenoid of formula (II) from a diterpenoid of formula (I) which is extracted from *D. hongkongense*, including a step of oxidatively degrading the diterpenoid of formula (I) with KMnO$_4$ and MgSO$_4$ in acetone to form the diterpenoid of formula (II).

The present invention further discloses a method for preparing a diterpenoid represented by formula (I), including steps of: (a) extracting a *D. hongkongense* plant with an ethanol solution to obtain an extract; (b) partitioning the extract between ethyl acetate (EtOAc) and water to form an EtOAc layer; (c) evaporating an organic solvent from the EtOAc layer to obtain an EtOAc residue; (d) partitioning the EtOAc residue between n-hexane-methanol-water to form a methanol/water (MeOH/H$_2$O) extract; and (e) chromatographing the MeOH/H$_2$O extract over a silicon gel column to obtain the diterpenoid of formula (I).

The present invention further discloses a pharmaceutical composition including an effective amount of diterpenoid which is extracted from *D. hongkongense*, and the diterpenoid is compounds 1, 8, 9, 10, 11, 12, 13 and 14 or a combination thereof.

The present invention further discloses a use of the above pharmaceutical composition being prepared a drug used for anti-virus, anti-inflammation or anti-cancer treatments.

The present invention further discloses a diterpenoid of formula (I) being extracted from *D. hongkongense*.

BRIEF DESCRIPTION OF THE DRAWINGS

The objectives and advantages of the present invention will become more readily apparent to those ordinarily skilled in the art after reviewing the following detailed descriptions and accompanying drawings.

DETAILED DESCRIPTION OF THE PREFERRED EMBODIMENTS

The present invention will now be described more specifically with reference to the following embodiments. It is to be noted that the following descriptions of preferred embodiments of this invention are presented herein for purpose of illustration and description only; they are not intended to be exhaustive or to be limited to the precise form disclosed.

The structures of the new compounds in the present invention were established by interpretation of spectroscopic data, especially two-dimensional nuclear magnetic resonance (2D NMR). The stereochemistry of the compounds was established by chemical correlation, and the configurations thereof were definitively confirmed by X-ray crystallographic analysis.

Melting points of the compounds were recorded on a Büchi® B540 melting point apparatus. Optical rotations were recorded on a JASCO DIP-1000 polarimeter. Infrared (IR) spectra were taken on a HORIBA® FT-720 spectrophotometer. The $^1$H and $^{13}$C NMR spectra as well as 2D NMR spectra (correlation spectroscopy (COSY), heteronuclear multiple-quantum correlation (HMQC), heteronuclear multiple-bond correlation (HMBC), and nuclear overhauser enhancement spectroscopy (NOESY)) were recorded in CDCl$_3$ on a Bruker AVX NMR spectrometer operating at 400 MHz for $^1$H and 100 MHz for $^{13}$C using the CDCl$_3$ solvent peak as the internal standard ($\delta_H$ 7.265, $\delta_C$ 77.0 ppm). Low-resolution electron ionization mass spectroscopy (EIMS) was recorded on a VG Quattro 5022 mass spectrometer. High-resolution electrospray ionization mass spectroscopy (HRESIMS) was measured on a JEOL HX 110 mass spectrometer. LiChrospher® Si 60 (5 μm, 250-10, Merck) and LiChrospher® 100 RP-18e (5 μm, 250-10, Merck) were used for normal phase-high performance liquid chromatography (NP-HPLC) and reversed phased HPLC (RP-HPLC) (Hitachi®, L-6250; flow rate 2 mL/min, UV detection at 254 nm), respectively.

Figure 1:
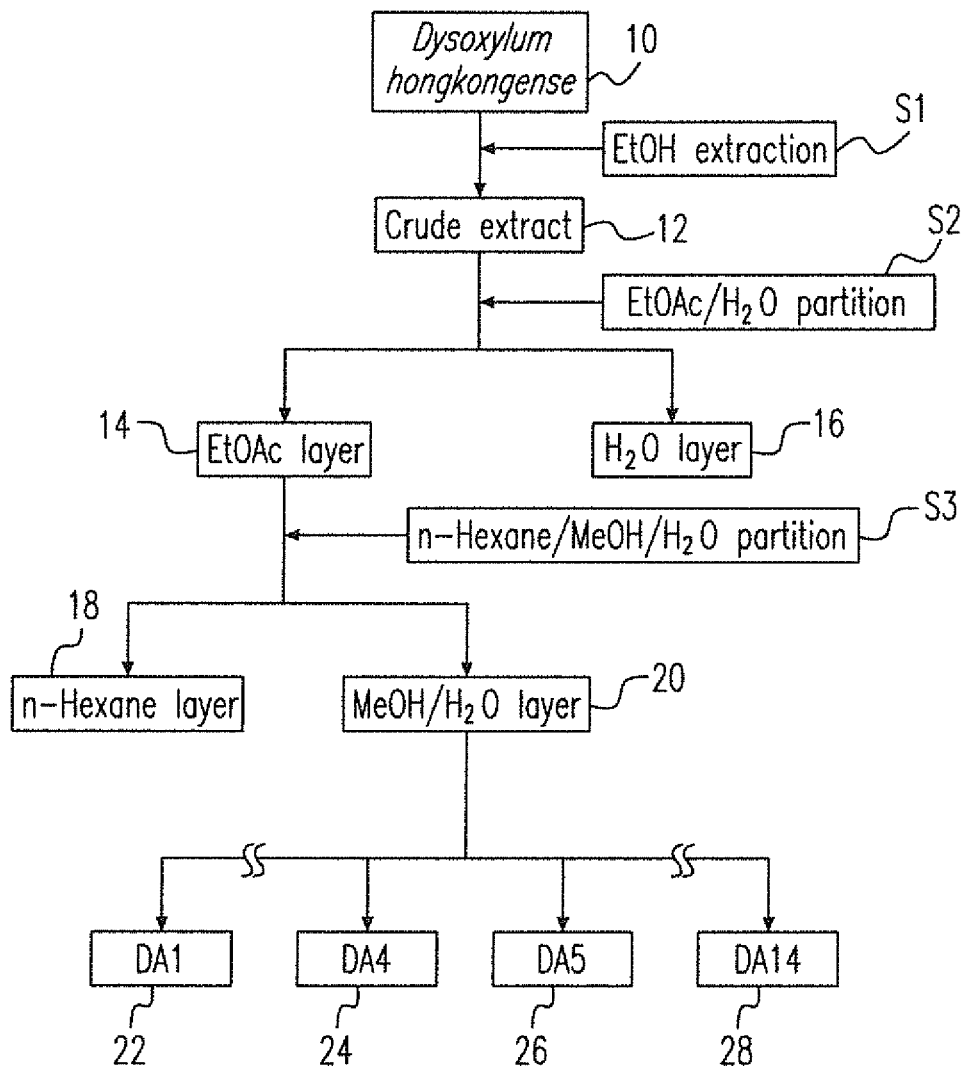
FIG. 1 is a flow chart showing that fractions DA1 to DA14 of the present invention are obtained by extracting *D. hongkongense*.

I. AMBROX® was obtained from the novel diterpenoid of formula (I) which was extracted from *Dysoxylum hongkongense*:

Please refer to the preparation method in FIG. 1, a plant of *D. hongkongense* 10 which was planted in Ping-Tong County, Taiwan was extracted with an ethanol solution (referring to step S1) to obtain a crude extract 12, which was partitioned between ethyl acetate (EtOAc) and water (referring to step S2) to form an EtOAc-soluble layer 14. After evaporating the organic solvent, the EtOAc residue was partitioned between n-hexane-methanol (MeOH)-water (referring to step S3) to create an EtOAc layer 18 and an MeOH/H$_2$O extract or MeOH/H$_2$O layer 20. The MeOH/H$_2$O layer was passed over an Si gel flash column to create a diterpenoid of formula (I) (Dysongensin A, compound 1). The above-ground part and root of the plant of *D. hongkongense* can be used for the extraction, and the above-ground part includes leaves, twigs or the like.

In detail, the air-dried leaves and twigs (2.7 kg) of *D. hongkongense* were ground and extracted three times with ethanol at room temperature and then concentrated under reduced pressure to create a crude extract (210 g). This crude extract was partitioned between EtOAc and H$_2$O (1:1) to obtain an EtOAc-soluble layer and a water layer (referring to block 16 in FIG. 1). After evaporating the organic solvent, the EtOAc residue (146 g) was partitioned between n-hexane-MeOH—H$_2$O (4:3:1) to create an MeO/H$_2$O extract. The MeOH/H$_2$O extract (86 g) was passed over an Si gel flash column (n-hexane-EtOAc, 1:0 to 0:1) to create fractions DA1 (block 22) to DA14 (block 28). Part (300 mg) of fraction DA4 (26.5 g, block 24) was subjected to NP-HPLC (n-hexane-EtOAc, 85:15-80:20) to create compound 1 (Dysongensin A, 98.4 mg, referring to FIG. 3) in fraction DA4-2, and a un-purified fraction DA4-6 was eluted with CH$_2$Cl$_2$—EtOAc (80:20) using NP-HPLC to create a compound 2 of formula (II) (3-ketoscareolide, 30.9 mg, referring to FIG. 3) in fraction DA4-6-2.

Compound 1 (Dysongensin A): off-white needles; mp 68-69° C., $[\alpha]_D^{25}$+29.2 (c 0.26, MeOH); UV (MeOH) $\lambda_{max}$ (log ε) 232 (4.60) nm; CD (c 0.06, MeOH) $[\theta]_{228}$+24038, $[\theta]_{255}$+1537, $[\theta]_{279}$+4741; IR (neat) $\nu_{max}$ 3455, 3086, 1702, 1638 cm$^{-1}$; $^1$H NMR (CDCl$_3$) and $^{13}$C NMR (CDCl$_3$) spectroscopic data, see Tables 1 and 3; HRESIMS m/z 327.2307 [M+Na]$^+$ (calcd for C$_{20}$H$_{32}$O$_2$Na, 327.2294).

The IR spectrum of compound 1 shows the presence of OH (3455 cm$^{-1}$), carbonyl (1702 cm$^{-1}$) and C=C double bond (3086, 1638 cm$^{-1}$) groups. The UV spectrum of compound 1 shows an absorption band at 232 nm, which implies the presence of a conjugated system in compound 1. The $^1$H NMR data of compound 1 (Table 1) exhibits signals of five methyl singlets (δ 0.92, 0.98, 1.04, 1.17 and 1.73) and four olefinic protons (δ 4.86, d, J=10.7 Hz, H-15a; 5.01, d, J=17.4 Hz, H-15b; 5.50, dd, J=7.1, 7.1 Hz; 6.27, H-12, dd, J=17.4, 10.7 Hz, H-14). An ABX spin system between H-15 and H-14 can be observed. The $^{13}$C NMR (Table 2) and the distortionless enhancement by the polariztion transfer (DEPT) spectra of compound 1 shows 20 carbon signals, consisting of a carbonyl carbon (δ 216.7), two double bonds (δ 110.4, 132.4, 135.1 and 141.1), an oxygenated quaternary carbon (δ 73.1), two aliphatic quaternary carbon (δ 38.1, 47.0), an aliphatic methine (δ 54.6), five aliphatic methylene (δ 20.9, 24.0, 33.6, 38.4, 42.9), and five methyl carbons (δ 11.6, 14.8, 20.9, 23.6, 26.4). In the COSY spectrum of compound 1, correlations between the olefinic protons H-14/H-15, and H-12/H-11 (δ 2.16, 2.39)/H-9 (δ 1.37), as well as methylenes H-1 (δ 1.49, 1.85)/H-2 (δ 2.36, 2.47) can be observed (data not shown). In the HMBC spectrum, correlations of H-15/C-13 (δ 132.4), Me-16/C-14, C-13, C-12, H-11/C-8, C-10 and H-12/C-9 (δ 60.6), C-14 (δ 141.1), indicated the presence of a conjugated double bond moiety, which was substituted at C-9. Two methyl groups attached to C-4 were revealed by the correlations of Me-18, Me-19/C-4 (δ 47.0), C-5 (δ 54.6), and the carbonyl carbon (C-3). The Me-17 methyl group was attached to C-8 as evidenced by the HMBC correlations of Me-17/C-8 (δ 73.1), C-9 and C-7. In addition, HMBC correlations of Me-20 (δ 0.92)/C-1 (δ 38.4), C-5, C-9 (δ 60.6), C-10, and H-7/C-5, C-6 (δ 20.9) as well as H-1/C-5 may construct a bicyclic ring system with a methyl group attached at C-10. The above 2D NMR reveals that compound 1 was a labdane type diterpene. Thus, the planar structure of compound 1 can easily be identified.

The relative configuration of compound 1 was elucidated on the basis of NOESY correlations. The NOESY spectrum of compound 1 shows correlations of Me-19/H-5, H-6α, Me-18/H-6β, H-20/H-2β, H-6β, H-11, Me-17, Me-17/H-6β, H-7β, H-11, H-5/H-7α, H-16/H-15β indicating that Me-17, Me-18 and Me-20 were on the β-face while Me-19, H-5 and H-9 were on the α-face of the molecule. Moreover, a strong NOESY correlation between H-12 and H-14 suggests that the double bond of C-12/C-13 was E-geometry. The CD spectrum of compound 1 shows a positive Cotton effect at 279 nm. Furthermore, compound 1 was reacted with $KMnO_4/MgSO_4$ in acetone to create a crystal product identical to compound 2, which was confirmed using X-ray crystallographic analysis (referring the following descriptions). The above reaction unambiguously established the structure of compound 1.

Compound 2 (3-Ketosclareolide): $[\alpha]_D^{25}$+10.7 (c 0.22, MeOH); CD (c 0.3, MeOH) $[\theta]_{214}$+2072, $[\theta]_{243}$+5, $[\theta]_{277}$+1056; IR (neat) $\nu_{max}$ 1773, 1702 cm$^{-1}$; $^1$H NMR (CDCl$_3$) and $^{13}$C NMR (CDCl$_3$) spectroscopic data, see Table 4; HRESIMS m/z 287.1631 [M+Na]$^+$ (calcd for $C_{16}H_{24}O_3Na$, 287.1623).

Figure 2:
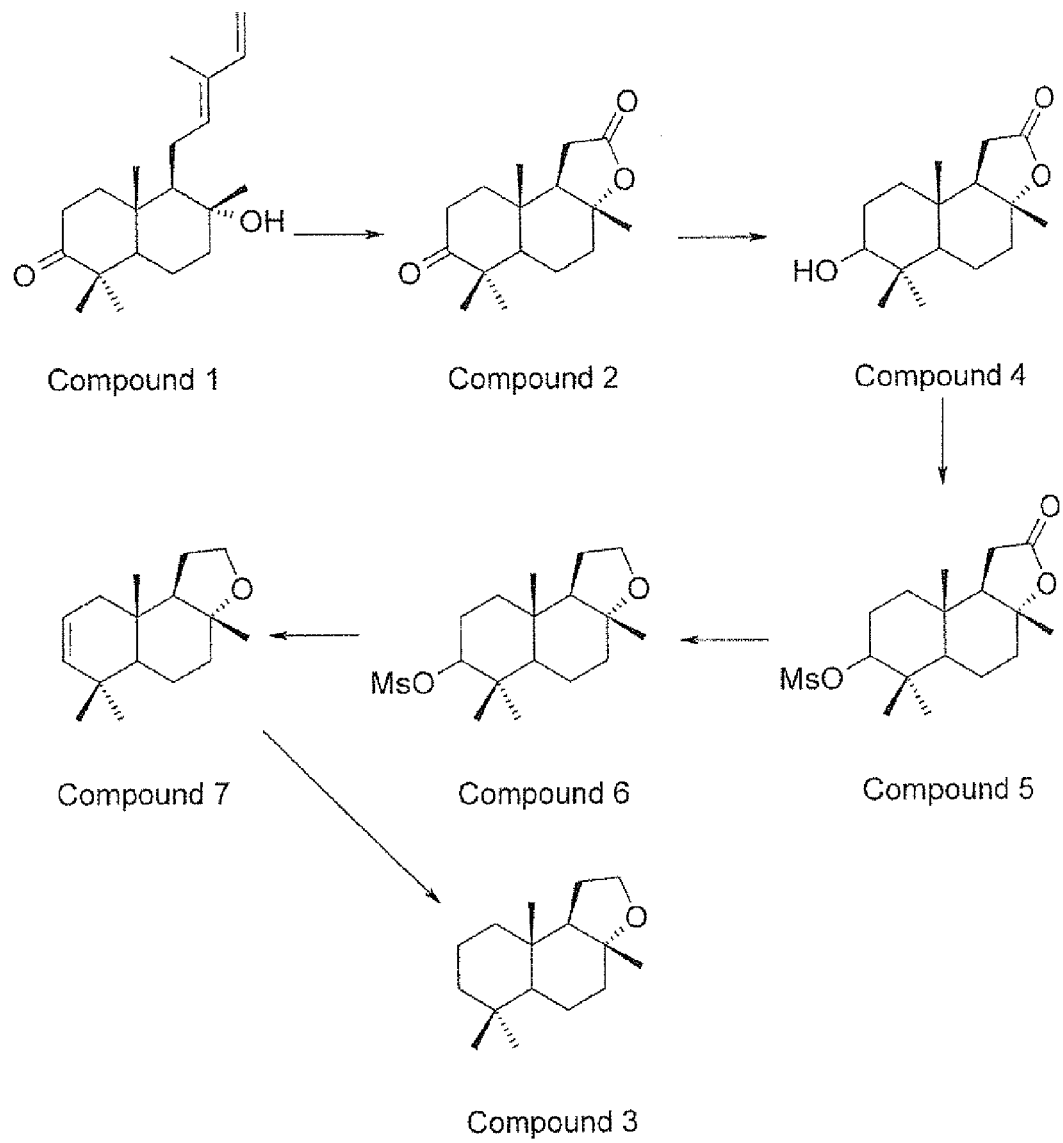
FIG. 2 is a flow chart showing that ambrox of the present invention is prepared from compound 1 which is extracted from *D. hongkongense*.

In addition to being obtained from D. hongkongense, compound 2 also can be obtained from compound 1 via oxidative cyclization. Please refer to FIG. 2, to a solution of compound 1 (200 mg, 0.656 mmol) in acetone (10 mL) was added potassium permanganate ($KMnO_4$, 311 mg, 1.97 mmol) and anhydrous magnesium sulfate ($MgSO_4$, 300 mg) at 0° C. After stirring for 15 minutes the reaction mixture was allowed to warm to room temperature and kept for 1 hour. The reaction mixture was filtered through celite, and the filtrate was concentrated under reduced pressure resulting a crude product, which was subjected to column chromatography eluted with hexane-ethyl acetate (3:2) to yield compound 2 of a white solid (158 mg, 91%). The spectroscopic data is identical to those in Table 4.

In one embodiment of the present invention, compound 2 can be synthesized from compound 1 which was extracted from D. hongkongense via the chemical reaction, and then compounds 4, 5, 6 and 7, as well as ambrox (compound 3) were sequentially prepared via a series of chemical reactions. Please refer to FIG. 2, compound 1 was treated with $KMnO_4$ and $MgSO_4$ in acetone, and the reaction proceeded through oxidative degradation of the 1,3-diene side chain followed by cyclization to create compound 2 having a lactone ring C. Further reduction of the ketone at the 3-position with $NaBH_4$ in dry methanol compound 2 created the corresponding compound 4 having a secondary alcohol structure. Then, compound 4 was protected as a mesylate by being treated with methanesulfonyl chloride in pyridine to create compound 5 having the mesylate structure. The reduction of compound 2 to create the corresponding compound 4 and the reductive removal of the mesylate group to hydrocarbon can be performed in a one-pot manner. Accordingly, compound 5 was treated with lithium aluminium hydride (LAH) in dry tetrahydrofuran (THF) followed by dehydrocyclization of the corresponding alcohol with a catalytic amount of p-toluenesulfonic acid (p-TsOH) in nitromethane. Compound 6 was treated with lithium chloride (LiCl) in DMF to create compound 7, which has an alkene structure between C-2 and C-3. Further hydrogenation of compound 7 using 10% palladium on carbon (Pd/C) catalyst in dry methanol yielded the desired AMBROX® (compound 3).

In another embodiment of the present invention, AMBROX® can be prepared from compound 2, which is extracted from D. hongkongense, via the chemical reactions described above.

The preparation method of compounds 4, 5, 6, 7 and 3 are described below.

Compound 4 (3-Hydroxy-sclareolide): To a solution of compound 2 (100 mg, 0.378 mmol) in methanol (4 mL) was added sodium borohydride ($NaBH_4$, 21 mg, 0.567 mmol) at 0° C. portion wise. After 10 minutes the reaction mixture warmed to room temperature and kept there for 30 minutes. The solvent was removed under reduced pressure and the resulting crude product was dissolved in EtOAc and washed with water. Then the organic layer was dried over $MgSO_4$ and the solvent was removed under vaccum. The crude product was purified by column chromatography using ethyl acetate/hexane (45-50%) to create compound 4 of a white solid (85 mg, 85%). $^1$H NMR (400 MHz, CDCl$_3$), δ 3.24 (dd, J=5.2, 10.8 Hz, 1H), 2.39 (t, J=15.6 Hz, 1H), 2.22 (dd, J=6.4, 16.0 Hz, 1H), 2.05-2.08 (m, 1H), 1.87-1.92 (m, 2H), 1.61-1.66 (m, 3H), 1.40-1.44 (m, 2H), 1.31 (s, 3H), 1.16 (dt, J=4.4, 12.8 Hz, 2H), 0.98 (s, 3H), 0.90 (s, 3H), 0.78 (s, 3H); $^{13}$C NMR (100 MHz, CDCl$_3$), δ 176.6, 86.2, 78.6, 58.9, 55.3, 38.8, 38.4, 37.7, 35.7, 28.7, 27.9, 26.8, 21.5, 20.3, 15.0, 15.1.

Compound 5 (3-Mesyloxy sclareolide): A solution of compound 4 (50 mg, 0.19 mmol) in pyridine (2 mL) was cooled to 0° C., and to that methansulfonyl chloride (21 µL 0.281 mmol) was added. The reaction mixture was stirred at the same temperature for 2 hours, and ethyl acetate was added. The mixture was washed with 5% HCl and brine and the organic layer was dried over $MgSO_4$, filtered, and concentrated in vacuo. The yellow residue was purified by column chromatography using ethyl acetate/hexane as an eluent to create compound 5 (63 mg 97%). $^1$H NMR (400 MHz, CDCl$_3$), δ 4.34 (dd, J=5.2, 11.6 Hz, 1H), 3.12 (s, 3H), 2.41 (t, J=15.6 Hz, 1H), 2.22 (dd, J=6.4, 16.0 Hz, 1H), 2.03-2.07 (m, 1H), 1.97-2.01 (m, 2H), 1.87-1.94 (m, 3H), 1.69 (dt, J=3.2, 12.4 Hz, 1H), 1.43-1.51 (m, 2H), 1.32 (s, 3H), 1.10-1.26 (m, 2H), 1.03 (s, 3H), 0.94 (s, 3H), 0.87 (s, 3H); $^{13}$C NMR (100 MHz, CDCl$_3$), δ 176.1, 89.0, 85.7, 58.6, 55.3, 38.9, 38.6, 38.2, 37.3, 35.5, 28.6, 28.0, 24.8, 21.5, 20.3, 15.9, 15.2.

Compound 6 (3-Mesyloxy ambrox): To a suspension of lithium aluminium hydride ($LiAlH_4$, 44 mg, 1.16 mmol) in THF (5 mL) was added compound 5 (100 mg 0.29 mmol) dissolved in 5 mL THF at 0° C. under an $N_2$ atmosphere. The reaction was heated to reflux for 2 hours and then cooled to 5° C. The reaction mixture was washed with water and filtered through celite and washed with ethyl acetate. The filtrate was concentrated under reduced pressure. Nitromethane (10 mL) and TsOH.H$_2$O (27 mg, 0.145 mmol) were directly added to the residue. This mixture was stirred at room temperature for 4 hours, then diluted with ethyl acetate, washed with a saturated $NaHCO_3$ solution and brine, dried over $MgSO_4$, and filtered. The filtrate was concentrated under reduced pressure and the crude product was purified with a silica gel column using ethyl hexane-ethyl acetate (3:2) as an eluent to create compound 6 (60 mg, 63%). $^1H$ NMR (400 MHz, $CDCl_3$), δ 4.34 (dd, J=6.2, 10.0 Hz, 1H), 3.89-3.94 (m, 1H), 3.83 (q, J=8.0 Hz, 1H), 3.02 (s, 3H), 1.95-2.03 (m, 3H), 1.71-1.76 (m, 3H), 1.55-1.58 (m, 1H), 1.31-1.40 (m, 2H), 1.21-1.26 (m, 3H), 1.08 (s, 3H), 1.03 (s, 3H), 0.87 (s, 3H); $^{13}C$ NMR (100 MHz, $CDCl_3$), δ 90.1, 79.6, 64.9, 59.8, 56.1, 39.3, 38.8, 38.6, 37.8, 35.7, 28.4, 25.1, 22.6, 21.0, 20.4, 16.0, 15.1.

Compound 7 ($\Delta^{2(3)}$-ambrox): To a solution of compound 6 (50 mg, 0.15 mmol) in DMF (7 mL) was added anhydrous LiCl (31 mg, 0.32 mmol). The mixture was stirred at 100° C. for 2 hours and then cooled to room temperature. Ethyl acetate was added, and the resulting solution was washed with water and brine, dried over $MgSO_4$ and filtered. The filtrate was concentrated under reduced pressure. The resulting crude product was purified over silica gel column using hexane-ethyl acetate (9:1) to create compound 7 (28 mg, 80%) as colorless oil. $^1H$ NMR (400 MHz, $CDCl_3$), δ 5.38-5.46 (m, 2H), 3.90-3.95 (m, 1H), 3.83 (q, J=8.4 Hz, 1H), 1.96-1.99 (m, 1H), 1.73-1.78 (m, 5H), 1.27-1.44 (m, 4H), 1.10 (s, 3H), 0.98 (s, 3H), 0.89 (s, 3H), 0.87 (s, 3H); $^{13}C$ NMR (100 MHz, $CDCl_3$), δ 138.6, 121.2, 79.8, 64.9, 58.8, 52.8, 40.5, 39.1, 35.2, 34,5, 31.9, 29.7, 22.7, 22.2, 21.5, 20.6, 15.2.

Compound 3 (AMBROX®): Palladium on carbon (Pd/C, 10%, 5 mg) was added to compound 7 (25 mg 0.11 mmol) in MeOOH (3 mL) and the resulting heterogeneous mixture was treated with $H_2$ at 1 atm. The reaction mixture was filtered through celite and the residue was washed with methanol. The methanol was removed by a vacuum to yield the desired compound 3 (23 mg, 92%). The NMR data were identical with those of Zoretic P. A. et al. (Synthesis of d,l-Norlabdane Oxide and Related Odorants: An Intramolecular Radical Approach. *J. Org. Chem.*, 1998, 63(14): 4779-4785.). $^1H$ NMR (400 MHz, $CDCl_3$), δ 3.88-3.93 (m, 1H), 3.82 (q, J=8.4 Hz, 1H), 1.92-1.95 (m, 1H), 1.68-1.75 (m, 3H), 1.37-1.48 (m, 5H), 1.17-1.27 (m, 2H), 1.10 (s, 3H), 0.94-1.08 (m, 3H), 0.87 (s, 3H), 0.83 (s, 6H); $^{13}C$ NMR (100 MHz, $CDCl_3$), δ 80.0, 65.0, 60.1, 57.3, 42.5, 40.0, 39.8, 36.2, 33.6, 33.1, 22.6, 21.2, 20.7, 18.4, 15.1.

II. A variety of novel diterpenoids extracted from *D. hongkongense*:

A variety of novel diterpenoids, including compounds 1, 2, 8, 9, 10, 11, 12, 13 and 14, can be extracted from the plant *D. hongkongense*.

The extraction methods of compounds 1 and 2 are described above and are not described again in this Section II.

Figure 3:
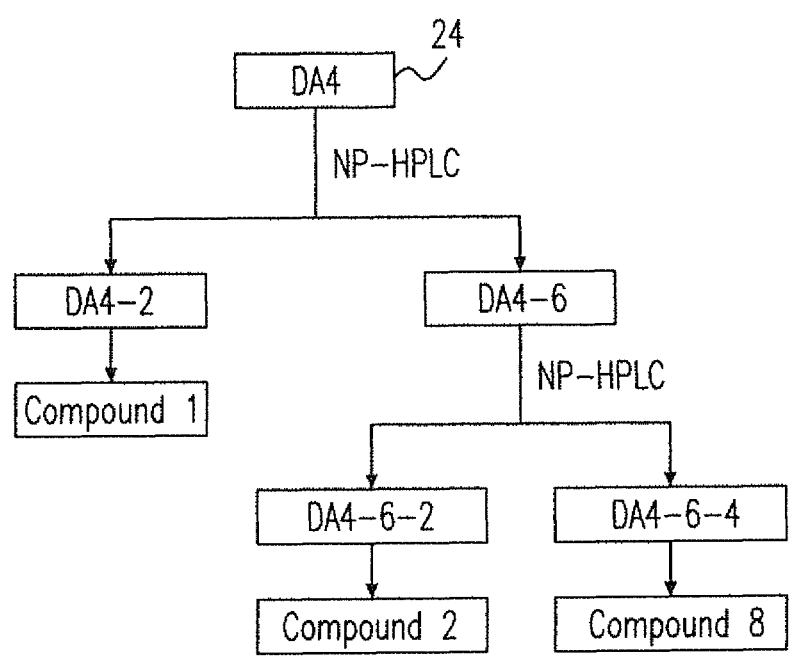
FIG. 3 is a flow chart showing that compounds 1 and 2 of the present invention are obtained from a fraction DA4.

In FIG. 3, fraction DA4-6 was subjected to NP-HPLC (dichloromethane-EtOAc, 80:20), and compound 8 (Dysongensin B, 6.5 mg) was obtained from fraction DA4-6-4.

Figure 4:
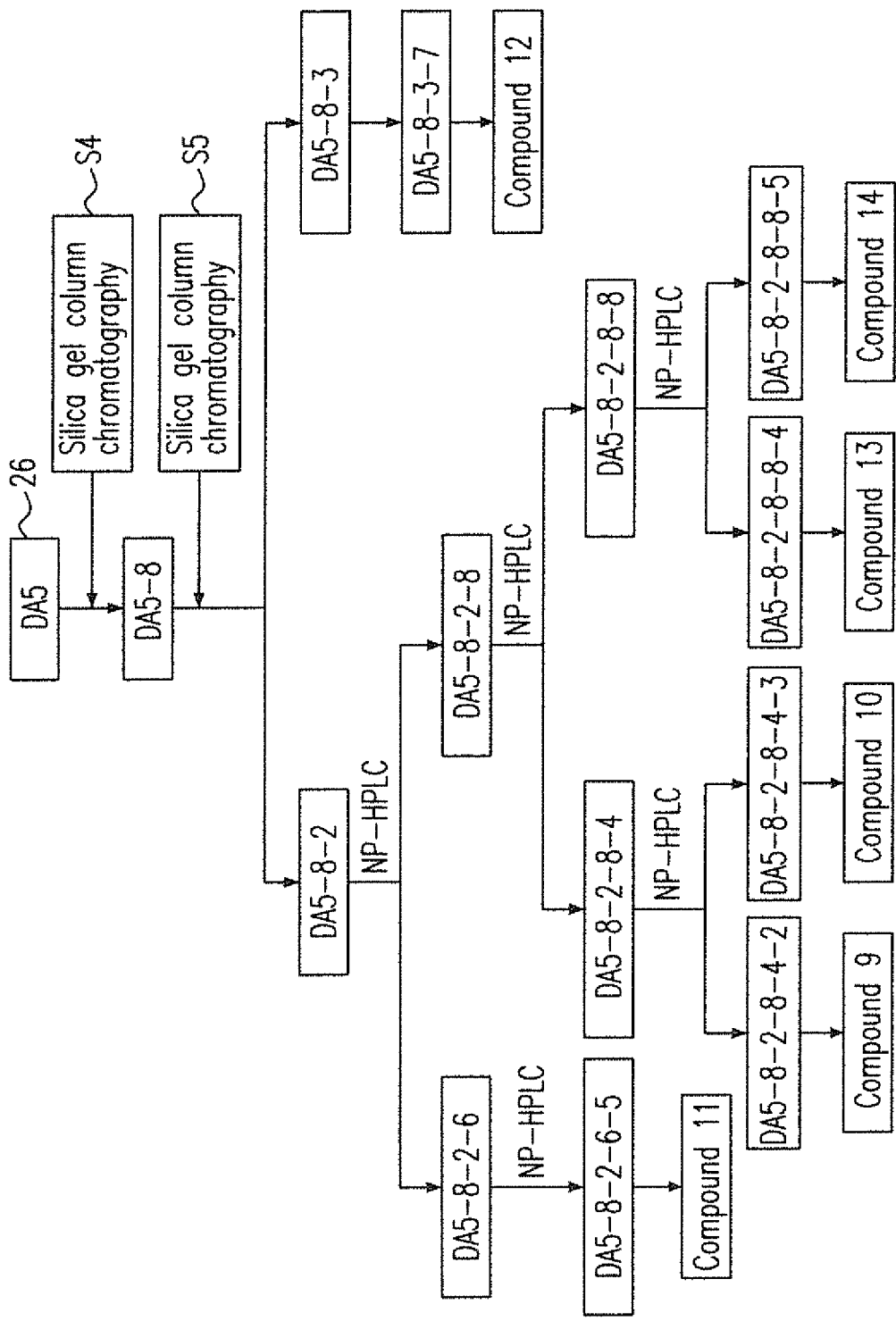
FIG. 4 is a flow chart showing that compounds 9 to 14 of the present invention are obtained from a fraction DA5.

In FIG. 4, fraction DA5 (6.2 g, block 26) was chromatographed on an Si gel column (step 54), isocratically eluted with n-hexane-EtOAc (85:15), eluted with 100% MeOH and detected with thin layer chromatography (TLC) to yield fraction DA5-8 (1.58 g), which was further separated with an Si gel column (step S5), isocratically eluted with n-hexane-acetone (4:1), eluted with 100% MeOH and detected with TLC to give fractions DA5-8-2 (1.07 g) and DA5-8-3 (312 mg). Fraction DA5-8-2 (1066 mg) was subjected to NP-HPLC (n-hexane-EtOAc, 65:35), the obtained fraction DA5-8-2-6 was subjected to NP-HPLC ($CH_2Cl_2$—EtOAc, 85:15) to create a new compound 11 (110 mg) from the obtained fraction DA5-8-2-6-5. Fraction DA5-8-2-8 was separated by NP-HPLC ($CH_2Cl_2$—EtOAc, 4:1), the obtained fraction DA5-8-2-8-4 was subjected to NP-HPLC (n-hexane-acetone, 85:15) to yield a new compound 9 (5.1 mg) from a given fraction DA5-8-2-8-4-2, and a new compound 10 (33.1 mg) from a given fraction DA5-8-2-8-4-3. Separation of fraction DA5-8-2-8-8 by NP-HPLC (n-hexane-acetone, 4:1) yielded a new compound 13 (7.0 mg) from a given fraction DA5-8-2-8-8-4 and a new compound 14 (9.7 mg) from a given fraction DA5-8-2-8-8-5. Fraction DA5-8-3 (312 mg) was separated by NP-HPLC (n-hexane-EtOAc, 55:45) to furnish a new compound 12 (14.2 mg) from a fraction DA5-8-3-7.

Compound 8 (Dysongensin B): off-white, amorphous powder; $[\alpha]_D^{25}$ 44.3 (c 0.26, MeOH); CD (c 0.15, MeOH) $[\theta]_{235}$+395, $[\theta]_{284}$+2357; IR (neat) $v_{max}$ 3455, 3082, 1702 $cm^{-1}$; $^1H$ NMR ($CDCl_3$) and $^{13}C$ NMR ($CDCl_3$) spectroscopic data, see Tables 1 and 3, respectively; HRESIMS m/z 343.2252 $[M+Na]^+$ (calcd for $C_{20}H_{32}O_3Na$, 343.2243).

The $^1H$ and $^{13}C$ NMR spectra of compound 8 were similar to those of compound 1, suggesting that it is a close analog of compound 1. The difference between them was that the chemical shifts of H-12 (δ 3.51), C-12 (δ 77.5) and C-13 (δ 76.6) in compound 8 were upfield shifted compared to those of compound 1 ($\delta_H$ 5.50; $\delta_C$ 135.1, 132.4), and the shift values of H-15 (δ 5.24, 5.43), C-15 (δ 117.4), C-8 ($\delta_H$ 75.4) and C-16 (δ 27.9) were downfield shifted compared to those of the same carbon in compound 1 ($\delta_H$ 4.86, 5.01; $\delta_C$ 110.0, 73.7, 11.8). Thus, it is suggested that the double bond between C-12 and C-13 was missing and an ether linkage was formed between C-8 and C-13. In addition, a hydroxyl group (OH) attached at C-12 was observed in compound 8. This was supported from the COSY (H-9/H-11/H-12) and HMBC correlations of H-16 (δ 1.80)/C-12, C-13, C-14 ($\delta_C$ 140.1) (not shown). The other COSY and HMBC correlations revealed that all the other structural fragments including the rings A and B were similar to those of compound 1, confirming that compound 8 belongs to a six membered cyclic ether derivative of compound 1.

NOESY correlations of Me-20 (δ 0.86)/H-11β (δ 1.57), Me-18 (δ 0.99), Me-17 (δ 1.27) and Me-17/H-14 of compound 8 indicated that Me-20, Me-17 and the vinyl group at C-13 were all β-oriented. On the other hand, NOESY cross peaks between H-9 (δ 1.33)/H-12, H-1α (δ 1.47) and H-12/H-11α (δ 1.77), Me-16 revealed that H-9, H-12 and Me-16 were α-oriented. The relative configurations at C-12 and C-13 were also determined as R. Furthermore, the positive Cotton effect at 284 nm in the CD spectrum of compound 8 also agreed with the same configuration as compound 1. Therefore, the structure of compound 8 was established.

Compound 9 (Dysongensin C): off-white prism; mp 85-86° C.; $[\alpha]_D^{25}$ 18.8 (c 0.51, MeOH); CD (c 0.4, MeOH) $[\theta]_{290}$+2096; IR (neat) $v_{max}$ 3480, 3088, 1702, 1641 $cm^{-1}$; $^1H$ NMR ($CDCl_3$) and $^{13}C$ NMR ($CDCl_3$) spectroscopic data, see Tables 1 and 3, respectively; HRESIMS m/z 343.2243 $[M+Na]^+$ (calcd for $C_{20}H_{32}O_3Na$, 343.2243).

The $^1H$ and $^{13}C$ NMR spectra of compound 9 revealed a tricyclic labdane pattern consisting of a vinyl group ($\delta_H$ 5.84, dd, J=17.4, 10.9 Hz; 5.10, dd, J=10.9, 1.7 Hz, H-15a; 5.28, dd, J=17.4, 1.7 Hz, H-15b), a carbonyl carbon ($\delta_C$ 216.7), five methyl protons ($\delta_H$ 0.92 s, 1.02 s, 1.09 s, 1.19 s, 1.30 s) and carbons ($\delta_C$ 25.9, 24.9, 20.7, 26,8, 15.3) similar to those of compound 8. However, the methine protons ($\delta_H$ 3.79, 5.84) at C-12 and C-14 and carbons of C-8 ($\delta_C$ 80.7), C-9 ($\delta_C$ 60.2), C-12 ($\delta_C$ 85.1), C-13 ($\delta_C$ 73.3) and C-15 ($\delta_C$ 113.6) were quite different from those of compound 8, suggesting that compound 9 might contain a pentacyclic ether in the C-ring. HMBC correlations of H-12/C-9, H-16 (δ 1.30)/C-12, C-14 (δ 140.9), H-15/C-13 and H-17/C-8 (δ 39.9) also support a tetrahydrofuran ring system with a methyl vinyl carbinol moiety attached at C-12. Assuming that H-9 of compound 9 is on the α-face same as compound 8, the NOESY correlations of H-12/H-9 revealed that H-12 is α-oriented. The configuration at C-12 and C-13 was thus elucidated as S and R respectively. An X-ray crystallographic analysis (not shown) unambiguously confirmed the configurations deduced by the NOESY experiment and also revealed that H-12 was located on the α-face. The positive Cotton effect at 290 nm in the CD spectrum of compound 9 is similar to those of compounds 1 and 8. On the basis of the above evidence, the structure of compound 9 was established.

Compound 10 (Dysongensin D): colorless, gum; $[\alpha]_D^{25}$ 24 (c 0.65, MeOH); CD (c 0.5, MeOH) $[\theta]_{234}$+37, $[\theta]_{292}$+233; IR (neat) $v_{max}$ 3455, 3085, 1701, 1644 cm$^{-1}$; $^1$H NMR (CDCl$_3$) and $^{13}$C NMR (CDCl$_3$) spectroscopic data, see Tables 1 and 3, respectively; HRESIMS m/z 343.2247 [M+Na]$^+$ (calcd for C$_{20}$H$_{32}$O$_3$Na, 343.2243).

The $^1$H and $^{13}$C NMR spectra of compound 10 contained characteristic signals of a tricyclic labdane pattern including the vinyl group ($\delta_H$ 5.93, dd, J=17.3, 10.7 Hz; 5.11, dd, J=10.7, 0.8 Hz, H-15a; 5.28, dd, J=17.3, 0.8 Hz, H-15b), a carbonyl carbon ($\delta_C$ 216.8), five methyl protons ($\delta_H$ 0.91 s, 1.02 s, 1.09 s, 1.16 s, 1.21 s) and carbons ($\delta_C$ 14.3, 20.7, 20.8, 23.6, 26.9). However, the methine proton ($\delta_H$ 3.79, J=7.9, 4.7 Hz) and carbon ($\delta_C$ 85.1) at C-12 were different from those of compound 9, suggesting that the configuration of C-12 in compound 10 may be different from that of compound 9. HMBC correlations H-12/C-9, C-13 and H-16 ($\delta$ 1.21)/C-12, C-14 ($\delta_C$ 142.8) also support the planar structure of the side chain in compound 10 (not shown). A NOESY correlation of H-12/Me-17 and no correlation observed between H-12 and H-9 agreed with the β-orientation of H-12. Therefore the configurations of compound 10 at C-12 and C-13 were elucidated as R and R respectively.

Compound 11 (Dysongensin E): off-white, amorphous powder; $[\alpha]_D^{25}$ 5.4 (c 0.85, MeOH); CD (c 0.6, MeOH) $[\theta]_{235}$+45, $[\theta]_{290}$+2144; IR (neat) $v_{max}$ 3473, 3085, 1701, 1644 cm$^{-1}$; $^1$H NMR (CDCl$_3$) and $^{13}$C NMR (CDCl$_3$) spectroscopic data, see Tables 2 and 3, respectively; HRESIMS m/z 343.2218 [M+Na]$^+$ (calcd for C$_{20}$H$_{32}$O$_3$Na, 343.2243).

The $^1$H and $^{13}$C NMR spectra of compound 11 were superimposable with those of compound 10 except that the signals of C-14 ($\delta$ 140.9) and C-16 ($\delta$ 24.6) were slightly different from those of compound 10. The same labdane system and the side chain at C-12 of compound 11 was determined by COSY (H-9/H-11/H-12 and H-14/H-15) and HMBC (H-12/C-16, C-9, C-14). The NOESY correlation between H-12 ($\delta$ 3.88) and Me-17 ($\delta$ 1.12) and absence of correlation between H-12 and H-9 ($\delta$ 1.33) clearly determined the configuration of H-12 of compound 11 as R. The carbon chemical shifts of compound 11 revealed the S configuration at C-13.

Compound 12 (Dysongensin F): off-white, amorphous powder; $[\alpha]_D^{25}$ -2.3 (c 1.42, MeOH); IR (neat) $v_{max}$ 3438, 3050, 1704, 1641 cm$^{-1}$; $^1$H NMR (CDCl$_3$) and $^{13}$C NMR (CDCl$_3$) spectroscopic data, see Tables 2 and 3, respectively; HRESIMS m/z 345.2413 [M+Na]$^+$ (calcd for C$_{20}$H$_{34}$O$_3$Na, 345.2400).

The carbonyl carbon in compound 11 was missing in compound 12. Instead, it was replaced by a methine proton at $\delta$ 3.20 (dd, 10.8, 5.5 Hz). Detailed comparison of the chemical shifts of H-2 ($\delta$ 1.55m, 1.61m), C-2 ($\delta$ 27.0), C-3 ($\delta$ 78.9) and C-4 ($\delta$ 55.9) of compound 12 with those of compound 11 revealed that compound 12 contained a hydroxyl at C-3. The COSY (H-1/H-2/H-3) and HMBC (H-1/C-3 and Me-18, Me-19/C-3) correlations also supported the planar structure of compound 12. The NOESY correlations of H-3/H-5, Me-19 determined the β-face of the C-3 hydroxyl group while correlations of H-12/Me-17, H-9/H-5 and Me-18/Me-20 agreed with the same configuration of C-5, C-9, C-10 and C-12 as compound 11. Comparison of carbon data of C-12 and C-13 of compound 12 with those of compound 11 also assigned the configuration of C-12 and C-13 as R and S respectively.

Compound 13 (Dysongensin G): off-white, amorphous powder; $[\alpha]_D^{25}$ 24.0 (c 0.70, MeOH); IR (neat) $v_{max}$ 3458, 3049, 1643 cm$^{-1}$; $^1$H NMR (CDCl$_3$) and $^{13}$C NMR (CDCl$_3$) spectroscopic data, see Tables 2 and 3, respectively; HRESIMS m/z 343.2243 [M+Na]$^+$ (calcd for C$_{20}$H$_{32}$O$_3$Na, 343.2243).

The IR absorption bands at 3458, 3049 and 1643 cm$^{-1}$ of compound 13 indicated the presence of hydroxyl and double bond functionalities. The $^1$H and $^{13}$C NMR DEPT spectra of compound 13, consisting of an AMX spin system of vinyl protons ($\delta$ 5.66, dd, J=17.4, 1.4 Hz; $\delta$ 5.19, dd, J=10.9, 1.4 Hz; $\delta$ 5.37, dd, J=17.4, 1.4 Hz) and carbons ($\delta$ 137.4, CH; $\delta$ 115.9, CH$_2$), were similar to those of compound 11, suggesting an analogue. However, only three methyl protons ($\delta$ 0.77s, 0.93s, 1.16s) and carbons ($\delta$ 11.2q, 21.2q, 23.1q) instead of 5 methyls were observed in compound 13. The characteristic signals at $\delta$ 0.44 (dd, 9.2, 4.0 Hz, H-19) and $\delta$ −0.04 (dd, 5.4, 4.0 Hz, H-19) inferred the presence of a cyclopropane moiety. This finding was supported by the observation of COSY correlations of H-2 ($\delta$ 1.66 and 1.92)/H-3/H-19 and the carbonyl carbon in compound 11 was missing in compound 13. Moreover, a pair of methylene doublets at $\delta$ 3.36 (J=11.2 Hz) and $\delta$ 3.78 (J=11.2 Hz) suggest that a hydroxy was attached at C-16. This was proven by HMBC correlations of H-12/C-16, C9, C-14. Detailed analyses of COSY and HMBC spectra of compound 13 led to the elucidation of the planar structure, in which carbon signals at $\delta$ 17.8, 15.7 and $\delta$ 22.9 were assigned for the cyclopropane (C-3, C-4 and C-19) ring while carbon signals at $\delta$ 81.5, 75.4 and $\delta$ 21.2 were assigned for C-12, C-13 and C-17, respectively. The relative configuration was determined by a NOESY experiment and comparison of carbon chemical shifts of compound 13 with those of compound 11. NOESY correlations of Me-18/Me-20/Me-17/H-12 and H-3/H-19β indicate that they were all β-oriented while NOESY correlations of H-5/H-9/H-19α accounted α-orientation of H-5 and H-9. As mentioned before, the CMR data of C-12, C-13 and C-14 could suggest the R configuration of C-12 and C-13.

Compound 14 (Dysongensin H): off-white, amorphous powder; $[\alpha]_D^{25}$ 35.9 (c 0.97, MeOH); IR (neat) $v_{max}$ 3449, 3048, 1644 cm$^{-1}$; $^1$H NMR (CDCl$_3$) and $^{13}$C NMR (CDCl$_3$) spectroscopic data, see Tables 2 and 3, respectively; HRESIMS m/z 343.2254 [M+Na]$^+$ (calcd for C$_{20}$H$_{32}$O$_3$Na, 343.2243).

The $^1$H and $^{13}$C NMR spectroscopic data of compound 14 showed three methyl protons ($\delta$ 0.81s, 0.93s, 1.23s) and carbons ($\delta$ 12.0q, 23.0q, 24.7q), and the characteristic signals of a cyclopropane ring ($\delta$ 0.54; 0.45, dd, 9.4, 4.0 Hz, H-19β; $\delta$ −0.04, dd, 5.6, 4.0 Hz, H-19α) as well as a hydroxyl methylene group ($\delta$ 3.37, J=11.1 Hz; $\delta$ 3.83, J=11.1 Hz; $\delta$ 69.9, C-16), suggests that compound 14 was an analogue of compound 13. Supported by COSY, HMQC and HMBC correlations, compounds 14 and 13 could have the same planar structure. The difference could be the configuration at C-12 ($\delta$ 85.4) and C-13 ($\delta$ 73.9), whose data have been assigned from HMQC and HMBC correlations of compound 14. Moreover, analysis of a NOESY experiment of compound 14 also pointed out an identical configuration as compound 13 except without a correlation between H-12 and Me-17, but a correlation between H-12 and H-9 was observed in compound 14. This finding indicates that H-12 was on the α-face. A comparison of the chemical shifts of C-14 ($\delta$ 136.9) and C-17

(24.7) as well as C-12 and C-13 of compound 14 with those of compound 13 and published data established the S configuration of C-12 and C-13.

III. Anti-virus, anti-inflammation and anti-cancer effect of the novel diterpenoids:

Anti Herpes Simplex Virus-1 (HSV-1) Assay, Cell Culture and Virus. Vero cells were cultured in minimal essential medium (MEM; GIBCO®, Grand Island, N.Y.) supplemented with 10% fetal calf serum (FCS; Hyclone™, Logan, Utah), 100 U/mL penicillin and 100 μg/mL streptomycin and incubated at 37° C. in a 5% $CO_2$ incubator. To prepare a stock of HSV-1 (KOS strain, VR-1493, ATCC), Vero cells were infected with HSV-1 at a multiplicity of infection points on three plaque forming units (PFU)/cell and harvested at 24 hours postinfection and centrifuged at 1500×g (Centrifuge 5810 R, Eppendorf) at 4° C. for 20 minutes. The supernatant was collected and stored at −70° C. for use.

Plaque Reduction Assay. The bioassay followed a procedure described previously (Kuo et al., Samarangenin B from *Limonium sinense* Suppresses Herpes Simplex Virus Type 1 Replication in Vero Cells by Regulation of Viral Macromolecular Synthesis. Antimicrob. Agents Chemother., 2002, 46(9): 2854-2864.). Vero cells ($3.5 \times 10^5$ cells/dish) were incubated with 100 PFU of HSV-1 and various compounds (100 μM) or acyclovir (2.5 μM, the positive control) were added to the cells. The viruses were adsorbed for 1 hour at 37° C. and 1% methylcellulose was added to each well. After 5 days, the virus plaques formed in Vero cells were counted by crystal violet staining. The activities of various compounds and acyclovir for inhibition of plaque formation were calculated.

Anti-inflammatory Assays, Inhibitory Effect on Superpxide Anion Generation and Elastase Release by Human Neutrophils. Neutrophils were obtained by means of dextran sedimentation and Ficoll centrifugation. Superoxide generation and elastase release were carried out according to a procedure described previously (Hwang et al., Inhibition of Superoxide Anion and Elastase Release in Human Neutrophils by 3'-Isopropoxychalcone via a cAMP-dependent Pathway. *Br. J. Pharmacol.*, 2006, 148(1): 78-87.; and Liaw et al., Frajunolides E-K, Briarane Diterpenes from *Junceella fragilis*. *J. Nat. Prod.*, 2008, 71(9): 1551-1556.). Superoxide anion production was assayed by monitoring the superoxide dismutase-inhibitable reduction of ferricytochrome c. Elastase release experiments were performed using MeO-Suc-Ala-Ala-Pro-Val p-nitroanilide as the elastase substrate.

Cytotoxic Assay. Human hepatocellular carcinoma Hep-G2, human colon adenocarcinoma WiDr and human laryngeal carcinoma Hep-2 were used as the targets for research, and an antitumor drug, mitomycin C, was the control. The effective dosage ($ED_{50}$, μg/mL) of the compounds on the cancer cell cytotoxicity was determined by the well-known cytotoxicity assay (3-(4,5-dimethylthiazol-2-yl)-2,5-diphenyltetrazolium bromide (MTT) assay) in the art.

The isolated compounds 1 and 8 to 14 were evaluated for their in vitro inhibitory activity against the HSV-1 virus. Compounds 9, 10, 13 and 14 showed moderate activity (32.7±4.0%, 25.2±6.0%, 29.3±9.0% and 29.7±6.0% inhibition, respectively) at 10 μM. The anti-inflammatory activities of compounds 1 and 8 to 14 were tested on superoxide anion generation and elastase release by human neutrophils in response to formylmethionylleucyl-phenylalanine plus dihydrocytochalasin B (FMLP/CB) at the concentration of 10 μg/mL. As a result, compounds 11 and 14 showed anti-inflammatory effects (31.29±6.67% and 25.33±4.04%) on elastase release and superoxide anion generation, respectively.

The isolated compounds 1 and 8 to 14 were evaluated for their in vitro cytotoxicity against cancer cells. Compounds 1, 8, 13 and 14 showed cytotoxic activity against Hep-G2 cells ($ED_{50}$ of 20.34±0.58, 18.05±0.58, 37.78±0.81 and 16.86±0.85 μg/mL, respectively), compounds 1, 8 and 14 showed the cytotoxic activity against WiDr cells ($ED_{50}$ of 18.67±0.56, 19.13±0.56 and 15.45±0.73 μg/mL, respectively), and compounds 8 and 12 showed the cytotoxic activity against Hep-2 cells ($ED_{50}$ of 16.07±0.17 and 17.92±0.25 μg/mL, respectively). Other compounds, compounds 9, 10 and 11, showed various cytotoxicities against Hep-G2, WiDr and Hep-2 carcinoma (not shown).

Because compounds 1, 8 and 14 belong to the diterpenoids having a similar main structure, compounds 1, 8 and 14 can be used for anti-virus, anti-inflammation or anti-cancer treatments, and can be prepared as pharmaceutical compositions and drugs.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

TABLE 1

$^1$H NMR Data (400 MHz) of Compounds 1, 8, 9 and 10[a]

| Position | 1 | 8 | 9 | 10 |
|---|---|---|---|---|
| 1α | 1.49 m | 1.47 m | 1.55 m | 1.55 m |
| 1β | 1.85 m | 1.89 ddd (13.0, 7.6, 4.4) | 1.75 m | 1.71 m |
| 2α | 2.36 m | 2.45 ddd (16.1, 7.8, 4.4) | 2.44 ddd (16.4, 7.7, 3.6) | 2.43 ddd (16.4, 7.7, 3.7) |
| 2β | 2.47 ddd (16.0, 10.4, 7.3) | 2.52 ddd (16.1, 7.8, 9.9) | 2.55 ddd (16.4, 7.7, 10.1) | 2.53 ddd (16.4, 7.7, 10.0) |
| 3 | | | | |
| 4 | | | | |
| 5 | 1.47 m | 1.50 m | 1.47 m | 1.46 m |
| 6β | 1.38 m | 1.43 m | 1.46 m | 1.45 m |
| 6α | 1.55 m | 1.61 m | 1.72 m | 1.69 m |
| 7α | 1.42 m | 1.39 m | 1.46 m | 1.42 m |
| 7β | 1.85 m | 1.83 m | 1.97 m | 1.98 m |
| 8 | | | | |
| 9 | 1.37 m | 1.33 dd (12.5, 1.7) | 1.54 m | 1.36 dd (12.0, 8.8) |
| 10 | | | | |
| 11α | 2.16 m | 1.77 ddd (12.5, 4.7, 1.7) | 1.56 m | 1.70 m |
| 11β | 2.39 m | 1.57 m | 1.69 m | 1.76 m |
| 12 | 5.50 t (7.1) | 3.51 dd (11.4, 4.7) | 3.79 dd (10.0, 5.4) | 3.94 dd (7.9, 4.7) |
| 13 | | | | |
| 14 | 6.27 dd (17.4, 10.7) | 6.29 dd (17.8, 11.3) | 5.84 dd (17.4, 10.9) | 5.93 dd (17.3, 10.7) |
| 15α | 4.86 d (10.7) | 5.24 dd (11.3, 1.1) | 5.10 dd (10.9, 1.7) | 5.11 dd (10.7, 0.8) |
| 15β | 5.01 d (17.4) | 5.43 dd (17.8, 1.1) | 5.28 dd (17.4, 1.7) | 5.28 dd (17.3, 0.8) |
| 16 | 1.73 s | 1.35 s | 1.30 s | 1.21 s |
| 17 | 1.17 s | 1.27 s | 1.19 s | 1.16 s |
| 18 | 0.98 s | 0.99 s | 1.02 s | 1.02 s |
| 19 | 1.04 s | 1.07 s | 1.09 s | 1.09 s |
| 20 | 0.92 s | 0.86 s | 0.92 s | 0.91 s |

[a]Chemical shifts are in ppm (δ); J values in Hz are in parentheses.

TABLE 2

¹H NMR Data (400 MHz) of Compounds 11, 12, 13 and 14[a]

| Position | 11 | 12 | 13 | 14 |
|---|---|---|---|---|
| 1α | 1.51 m | 1.11 m | 0.76 m | 0.70 m |
| 1β | 1.65 m | 1.42 ddd (13.1, 3.5, 3.5) | 1.35 m | 1.39 m |
| 2α | 2.38 ddd (16.3, 7.7, 3.7) | 1.55 m | 1.66 m | 1.67 m |
| 2β | 2.48 ddd (16.3, 7.7, 10.1) | 1.61 m | 1.92 m | 1.94 m |
| 3 |  | 3.20 dd (10.8, 5.5) | 0.53 m | 0.54 m |
| 4 |  |  |  |  |
| 5 | 1.43 m | 0.87 m | 0.90 m | 0.87 dd (12.5, 3.6) |
| 6β | 1.41 m | 1.33 m | 1.46 m | 1.46 m |
| 6α | 1.65 m | 1.74 m | 1.86 m | 1.87 m |
| 7α | 1.40 m | 1.35 m | 1.39 m | 1.40 m |
| 7β | 1.92 m | 1.92 m | 1.90 m | 1.90 m |
| 8 |  |  |  |  |
| 9 | 1.33 m | 1.28 dd (12.9, 7.6) | 1.22 dd (13.2, 7.4) | 1.23 dd (13.8, 5.1) |
| 10 |  |  |  |  |
| 11α | 1.60 m | 1.58 m | 1.59 m | 1.52 m |
| 11β | 1.68 m | 1.64 m | 1.74 m | 1.79 m |
|  | 3.88 dd (9.0, 3.6) | 3.89 dd (12.9, 7.6) | 4.14 dd (9.3, 3.4) | 3.98 dd (10.0, 5.8) |
| 12 |  |  |  |  |
| 13 |  |  |  |  |
| 14 | 5.81 dd (17.4, 10.9) | 5.84 dd (17.4, 10.9) | 5.66 dd (17.4, 1.4) | 5.65 dd (17.4, 10.9) |
| 15α | 5.07 dd (10.9, 1.5) | 5.10 dd (10.9, 1.3) | 5.19 dd (10.9, 1.4) | 5.17 dd (10.9, 1.6) |
| 15β | 5.22 dd (17.4, 1.5) | 5.25 dd (17.4, 1.3) | 5.37 dd (17.4, 1.4) | 5.40 dd (17.4, 1.6) |
| 16 | 1.21 s | 1.23 s | 3.36 d (11.2) 3.78 d (11.2) | 3.37 d (11.1) 3.83 d (11.1) |
| 17 | 1.12 s | 1.11 s | 1.16 s | 1.23 s |
| 18 | 0.97 s | 0.76 s | 0.93 s | 0.93 s |
| 19 | 1.05 s | 0.96 s | 0.44 dd (9.2, 4.0) −0.04 dd (5.4, 4.0) | 0.45 dd (9.4, 4.0) −0.04 dd (5.6, 4.0) |
| 20 | 0.86 s | 0.78 s | 0.77 s | 0.81 s |

[a]Chemical shifts are in ppm (δ); J values in Hz are in parentheses.

TABLE 3

¹³C NMR Data (100 MHz) of Compounds 1 and 8 to 14[a]

| Position | 1 | 8 | 9 | 10 | 11 | 12 | 13 | 14 |
|---|---|---|---|---|---|---|---|---|
| 1 | 38.4 (CH₂) | 38.0 (CH₂) | 38.1 (CH₂) | 38.0 (CH₂) | 37.8 (CH₂) | 37.8 (CH₂) | 35.5 (CH₂) | 35.9 (CH₂) |
| 2 | 33.6 (CH₂) | 33.7 (CH₂) | 33.7 (CH₂) | 33.7 (CH₂) | 33.6 (CH₂) | 27.0 (CH₂) | 18.4 (CH₂) | 18.5 (CH₂) |
| 3 | 216.7 (C) | 217.1 (C) | 216.7 (C) | 216.8 (C) | 216.7 (C) | 78.9 (CH) | 17.8 (CH) | 17.7 (CH) |
| 4 | 47.0 (C) | 47.2 (C) | 47.3 (C) | 47.3 (C) | 47.1 (C) | 38.7 (C) | 15.7 (C) | 15.8 (C) |
| 5 | 54.6 (CH) | 54.3 (CH) | 54.9 (CH) | 55.1 (CH) | 54.9 (CH) | 55.9 (CH) | 52.5 (CH) | 52.5 (CH) |
| 6 | 20.9 (CH₂) | 20.8 (CH₂) | 22.4 (CH₂) | 21.6 (CH₂) | 21.5 (CH₂) | 20.2 (CH₂) | 24.3 (CH₂) | 25.0 (CH₂) |
| 7 | 42.9 (CH₂) | 41.4 (CH₂) | 39.9 (CH₂) | 38.7 (CH₂) | 38.5 (CH₂) | 39.3 (CH₂) | 38.9 (CH₂) | 39.9 (CH₂) |
| 8 | 73.1 (C) | 75.4 (C) | 80.7 (C) | 80.9 (C) | 80.8 (C) | 81.3 (C) | 81.9 (C) | 81.8 (C) |
| 9 | 60.6 (CH) | 56.9 (CH) | 60.2 (CH) | 59.4 (CH) | 59.1 (CH) | 59.9 (CH) | 57.2 (CH) | 57.2 (CH) |
| 10 | 38.1 (C) | 36.4 (C) | 35.9 (C) | 35.9 (C) | 35.7 (C) | 35.9 (C) | 34.9 (C) | 35.0 (C) |
| 11 | 24.0 (CH₂) | 25.4 (CH₂) | 24.4 (CH₂) | 23.9 (CH₂) | 24.1 (CH₂) | 24.2 (CH₂) | 24.7 (CH₂) | 24.3 (CH₂) |
| 12 | 135.1 (CH) | 77.5 (CH) | 85.1 (CH) | 81.4 (CH) | 81.3 (CH) | 81.5 (CH) | 81.5 (CH) | 85.4 (CH) |
| 13 | 132.4 (C) | 76.6 (C) | 73.3 (C) | 74.4 (C) | 74.3 (C) | 74.5 (C) | 75.4 (C) | 73.9 (C) |
| 14 | 141.1 (CH) | 140.1 (CH) | 140.9 (CH) | 142.8 (CH) | 140.9 (CH) | 141.1 (CH) | 137.4 (CH) | 136.9 (CH) |
| 15 | 110.4 (CH₂) | 117.4 (CH₂) | 113.6 (CH₂) | 113.0 (CH₂) | 113.6 (CH₂) | 113.6 (CH₂) | 115.9 (CH₂) | 115.7 (CH₂) |
| 16 | 11.6 (CH₃) | 27.9 (CH₃) | 25.9 (CH₃) | 23.6 (CH₃) | 24.6 (CH₃) | 24.9 (CH₃) | 69.4 (CH₂) | 69.9 (CH₂) |
| 17 | 23.6 (CH₃) | 24.9 (CH₃) | 24.9 (CH₃) | 20.7 (CH₃) | 20.8 (CH₃) | 21.3 (CH₃) | 21.2 (CH₃) | 24.7 (CH₃) |
| 18 | 20.9 (CH₃) | 20.8 (CH₃) | 20.7 (CH₃) | 20.8 (CH₃) | 20.6 (CH₃) | 15.1 (CH₃) | 23.1 (CH₃) | 23.0 (CH₃) |
| 19 | 26.4 (CH₃) | 26.6 (CH₃) | 26.8 (CH₃) | 26.9 (CH₃) | 26.8 (CH₃) | 28.1 (CH₃) | 22.9 (CH₃) | 22.9 (CH₃) |
| 20 | 14.8 (CH₃) | 15.6 (CH₃) | 15.3 (CH₃) | 14.3 (CH₃) | 14.1 (CH₃) | 14.8 (CH₃) | 11.2 (CH₃) | 12.0 (CH₃) |

[a]Assignments were made using HMQC and HMBC techniques.

TABLE 4

¹H and ¹³C NMR spectroscopic data of compound 2

| Position | ¹H[a] | ¹³C[b] |
|---|---|---|
| 1 | 1.59 m 1.70 m | 37.6 (CH₂) |
| 2 | 2.46 ddd (16.5, 7.8, 3.3) 2.55 ddd (16.5, 7.8, 10.1) | 33.3 (CH₂) |
| 3 |  | 215.4 (C) |
| 4 |  | 47.3 (C) |
| 5 | 1.59 m | 54.3 (CH) |
| 6 | 1.52 m 1.81 m | 21.4 (CH₂) |
| 7 | 1.69 m 2.10 ddd (12.0, 3.3, 3.3) | 37.7 (CH₂) |
| 8 |  | 85.6 (C) |
| 9 | 1.97 dd (14.8, 6.5) | 58.1 (CH) |
| 10 |  | 35.5 (C) |
| 11 | 2.26 dd (16.2, 6.5) 2.44 dd (16.2, 14.8) | 28.6 (CH₂) |
| 12 |  | 175.9 (C) |
| 13 | 1.35 s | 21.1 (CH₃) |
| 14 | 1.09 s | 14.5 (CH₃) |
| 15 | 1.03 s | 26.6 (CH₃) |
| 16 | 0.99 s | 20.6 (CH₃) |

[a]Measured at 400 MHz, j value in Hz

[b]Measured at 100 MHz

What is claimed is:

1. A method for preparing (−)-8,12-epoxy-13,14,15,16-tetranorlabdane, comprising steps of:

(a) providing a diterpenoid represented by formula (I):

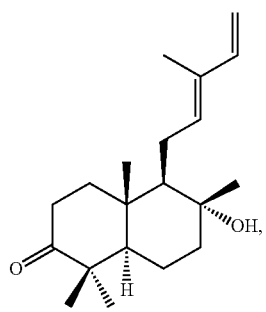

formula (I)

wherein the diterpenoid of formula (I) is extracted from a *Dysoxylum hongkongense*, (b) oxidatively transforming the diterpenoid of formula (I) to form the diterpenoid of formula (II):

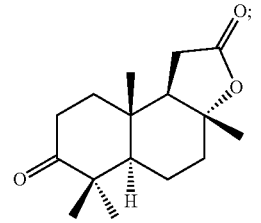

formula (II)

(c) reducing the diterpenoid of formula (II) with sodium borohydride to form 3-hydroxy-sclareolide;
(d) reacting the 3-hydroxy-sclareolide with methanesulfonyl chloride to form 3-mesyloxy sclareolide;
(e) reacting the 3-mesyloxy sclareolide with lithium aluminium hydride followed by dehydrocyclization using p-toluenesulfonic acid (TsOH.H$_2$O) in nitromethane to form 3-mesyloxy ambrox;
(f) reacting the 3-mesyloxy ambrox with lithium chloride to form a $\Delta^{2(3)}$-ambrox; and
(g) treating the $\Delta^{2(3)}$-ambrox with hydrogen gas to form the (−)-8,12-epoxy-13,14,15,16-tetranorlabdane.

2. The method according to claim 1, wherein in step (b), the diterpenoid of formula (I) is oxidatively transformed in acetone containing potassium permanganate and anhydrous magnesium sulfate.

3. The method according to claim 1, wherein step (c) is performed by adding the sodium borohydride to a methanol solution containing the diterpenoid of formula (II).

4. The method according to claim 1, wherein step (d) is performed by adding the methanesulfonyl chloride to a pyridine solution containing the 3-hydroxy-sclareolide.

5. The method according to claim 1, wherein in step (e), the 3-mesyloxy sclareolide is dissolved in a first tetrahydrofuran solution, and the lithium aluminium hydride is dissolved in a second tetrahydrofuran solution.

6. The method according to claim 1, wherein step (f) is performed by adding the lithium chloride to a dimethylformamide solution of the 3-mesyloxy ambrox.

7. The method according to claim 1, wherein in step (g), the $\Delta^{2(3)}$-ambrox is dissolved in a methanol solution, step (g) is performed by adding palladium on carbon to the methanol solution containing the $\Delta^{2(3)}$-ambrox, and the hydrogen gas has a pressure of 1 atm.

8. A method for preparing a diterpenoid represented by formula (I):

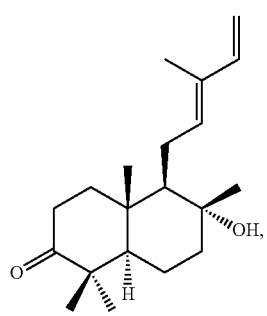

formula (I)

comprising steps of:
(a) extracting a *Dysoxylum hongkongense* plant with an ethanol solution to obtain an extract;
(b) partitioning the extract between ethyl acetate and water to form an ethyl acetate layer;
(c) evaporating organic solvent from the ethyl acetate layer to obtain an ethyl acetate residue;
(d) partitioning the ethyl acetate residue between n-hexane-methanol-water to form a methanol/water (MeOH/H$_2$O) extract; and
(e) chromatographing the MeOH/H$_2$O extract over a silica gel column to obtain the diterpenoid of formula (I).

9. The method according to claim 8, wherein the plant has an above-ground part and a root, and wherein at least one of which is used for the extraction.

10. The method according to claim 9, wherein the above-ground part is one of leaves and twigs.

* * * * *